United States Patent [19]

Friebe et al.

[11] 4,243,807

[45] Jan. 6, 1981

[54] 4-PHENOXYMETHYL-PIPERIDINES

[75] Inventors: Walter-Gunar Friebe, Darmstadt; Max Thiel, Mannheim, both of Fed. Rep. of Germany; Kurt Stach, deceased, late of Mannheim-Waldhof, Fed. Rep. of Germany; by Werner Plattner, administrator, Linz, Austria

[73] Assignee: Boehringer Mannheim GmbH, Mannheim-Waldhof, Fed. Rep. of Germany

[21] Appl. No.: 737,518

[22] Filed: Nov. 1, 1976

[30] Foreign Application Priority Data

Nov. 7, 1975 [DE] Fed. Rep. of Germany ....... 2549999

[51] Int. Cl.$^3$ ............................................ C07D 211/22
[52] U.S. Cl. .................................... 546/232; 544/277; 546/226; 546/236; 546/338; 546/339
[58] Field of Search ................... 260/293.83; 546/232, 546/236

[56] References Cited

U.S. PATENT DOCUMENTS 3,709,892  1/1973  Leeming et al. ................ 260/293.83

OTHER PUBLICATIONS

Chemical Abstracts, 73, 66442j (1970).

*Primary Examiner*—Henry R. Jiles
*Assistant Examiner*—Richard A. Schwartz
*Attorney, Agent, or Firm*—Sprung, Felfe, Horn, Lynch & Kramer

[57] ABSTRACT

4-Phenoxymethyl-piperidines of the formula

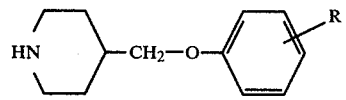

wherein R is hydrogen, halogen, nitro, lower alkyl or lower alkoxy, in the form of the free base or an acid addition salt, are provided and they are useful as intermediates in the production of anti-hypertensive agents through condensation with (a) propyl chloride and then with an adenine, or (b) a propyl indole.

12 Claims, No Drawings

4-PHENOXYMETHYL-PIPERIDINES

The present invention is concerned with new piperidine derivatives and with the preparation thereof.

The new piperidine derivatives according to the present invention are compounds of the general formula

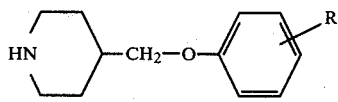   (I), wherein R is a hydrogen or halogen atom or a nitro group or a lower alkyl or alkoxy radical. The compounds may be present as the free piperidines or in the form of salts with inorganic and organic acids.

We have found that the new compounds of general formula (I) are valuable intermediates for the preparation of compounds with useful pharmaceutical properties, for example, with anti-allergic, circulatory-influencing (for example hypotensive) and central nervous system-depressing action. Thus, for example, by the reaction of compounds of general formula (I) with 1-bromo-3-chloropropane, there are obtained the corresponding 3-(4-phenoxymothylpiperidino)-propyl chlorides, reaction of which with adenine gives anti-allergically-effective 9-[3-(4-phenoxymothylpiperidino)-propyl]-adenines.

The new compounds of general formula (I) according to the present invention can be prepared, for example, by one of the following methods:

(a) hydrogenation of a phenoxymethylpyridine derivative of the general formula

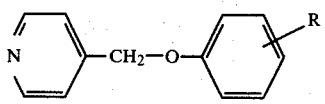   (II)

wherein R has the same meaning as above, or of an acid addition salt thereof; or (b) hydrolysis in an acidic or basic medium of an N-substituted 4-phenoxymethylpiperidine derivative of the general formula

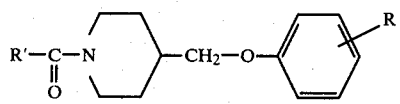   (III), wherein R has the same meaning as above and R' is an optionally substituted lower alkyl or aryl radical or a lower alkoxy or aryloxy radical; or (c) reaction of a piperidine derivative of the general formula

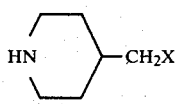   (IV), or of an acid addition salt thereof, with a benzene derivative of the general formula

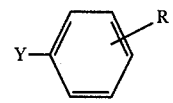   (V), wherein R has the same meaning as above, one of the symbols X and Y represents a hydroxyl group, whereas the other represents a reactive residue; whereafter the base obtained is, if desired, converted into an acid addition salt or a salt obtained is, if desired, converted into the free base.

The preferred halogen derivatives according to the present invention are the fluoro, chloro and bromo compounds.

The reactive residue X or Y can be, for example, a chlorine or bromine atom or a mesyloxy or tosyloxy radical.

The lower alkyl moieties of R and R' can be straight-chained or branched and contain up to 6 and preferably up to 4 carbon atoms.

Apart from the compounds mentioned in the following Examples, the present invention is, in particular, also concerned with compounds which have all the possible combinations of the substituents mentioned in the Examples.

The hydrogenation of compounds of general formula (II) is preferably carried out in an organic solvent with proton catalysis, for example, in a hydrogen halide-containing lower alcohol, preferably in methanolic hydrogen chloride solution, or in acetic acid solution, in the presence of a noble metal catalyst, for example, a platinum catalyst, preferably platinum oxide, at a temperature of from 10° to 50° C. and preferably at ambient temperature and at a hydrogen pressure of from 0.5 to 5 ats, preferably at atmospheric pressure.

Hydrolysis of compounds of general formula (III) is preferably carried out in an organic solvent, such as a lower alcohol, preferably in methanol or ethanol, or in a cyclic ether, for example, dioxane or tetrahydrofuran, in the presence of a mineral acid or of an excess of an alkali metal hydroxide at a temperature of from 20° C. to reflux temperature.

The reaction of compounds of general formula (IV) with those of general formula (V) is preferably carried out in an alkaline medium, for example in a lower alcohol in the presence of an alkali metal hydroxide or of an alkali metal alcoholate, at a reaction temperature of from 20° C. to reflux temperature.

The novel piperidines can be produced and/or used in subsequent reactions in the form of their free bases or as salts thereof with inorganic or organic acids. The bases can be converted to salts by addition of acids to solutions followed by suitable isolation or the salts can be treated with alkali, e.g. NaOH, to form the free bases. Where salts are involved, those with pharmacologically compatible acids are preferred but, since the acid anion may be removed prior to further conversion, this is not essential. Representative acids include hydrochloric acid, sulfuric acid, phosphoric acid, hydrobromic acid, acetic acid, lactic acid, citric acid, malic acid, salicylic acid, malonic acid, maleic acid or succinic acid.

EXAMPLE 1

4-Phenoxymethylpiperidine (a) Variant I:

(i) The 4-phenoxymethylpyridine used as starting material is obtained as follows:

A mixture of 37.0 g (0.25 mole) of 4-hydroxymethylpyridine hydrochloride and 150 ml of thionyl chloride is heated under reflux for 2 hours. After cooling, 250 ml of benzene are added to the reaction mixture, followed by filtering and washing the precipitate with benzene. There are obtained 32.0 g of 4-chloromethylpyridine hydrochloride (76% of theory); m.p. 171°–172° C.

To a solution of 3.5 g (0.15 mole) of sodium in 100 ml of methanol are added 14.1 g (0.15 mole) of phenol. The reaction mixture is evaporated, mixed with 50 ml of N,N-dimethyl formamide and 8.2 g (0.05 mole) of 4-chloromethylpyridine hydrochloride and the reaction mixture heated for 20 hours at 100° C. After cooling, the reaction mixture is mixed with diethyl ether, washed with a dilute aqueous solution of sodium hydroxide and with water, dried over anhydrous sodium sulfate, evaporated and the residue distilled in a vacuum. There are obtained 8.2 g of 4-phenoxymethylpyridine (88% of theory); b.p. 115°–117° C./0.1 mm Hg.

(ii) A mixture of 18.5 g (0.1 mole) of 4-phenoxymethylpyridine, 250 ml of methanol, 250 ml of 3 N methanolic hydrogen chloride solution and 2 g of platinum oxide is shaken at ambient temperature under a hydrogen pressure of 1 atmosphere absolute. After the take up of the calculated amount of hydrogen, the catalyst is filtered off, the filtrate is evaporated in a vacuum and the residue is recrystallized from ethanol. There are obtained 12.0 g of 4-phenoxymethylpiperidine hydrochloride (53% of theory); m.p. 218°–219° C. The free base is obtained by treating the hydrochloride with an aqueous solution of sodium hydroxide.

(b) Variant II:

(i) The N-benzoyl-4-phenoxymethylpiperidine used as starting material is obtained as follows:

4-Hydroxymethylpyridine is hydrogenated in methanol at 140° C. under 200 atmospheres of hydrogen pressure in the presence of ruthenium oxide, producing 4-hydroxymethylpiperidine, b.p. 126°–130° C./14 mm Hg; m.p. 55°–56° C. Reaction with benzoyl chloride produces N-benzoyl-4-hydroxymethylpiperidine (m.p. 83°–85° C.). A mixture of 135.0 g of N-benzoyl-4-hydroxymethyl-piperidine, 90 ml of thionyl chloride and 900 ml of chloroform is heated under reflux for 4 hours. Thereafter, the reaction mixture is mixed with water, while cooling with ice, and the organic phase is washed neutral with an aqueous solution of sodium bicarbonate, dried over anhydrous sodium sulfate and evaporated. There are obtained 132.0 g (90% of theory) of N-benzoyl-4-chloromethylpiperidine; m.p. 68°–70° C.

To a mixture of 28 ml of 30% sdium methanolate solution and 50 ml of methanol are added 14.1 g (0.15 mole) of phenol. The reaction mixture is evaporated in a vacuum and the residue is taken up in 120 ml of N,N-dimethyl formamide, 35.5 g (0.15 mole) of N-benzoyl-4chloromethylpiperidine are added thereto and the reaction mixture is stirred for 12 hours at 60°–70° C. After cooling, the reaction mixture is mixed with diethyl ether, washed with water and dilute aqueous sodium hydroxide solution, dried over anhydrous sodium sulfate and evaporated in a vacuum. The oily residue is triturated with diethyl ether/ligroin. There are obtained 23.0 g of N-benzoyl-4-phenoxymethylpiperidine (52% of theory); m.p. 95°–96° C.

(ii) A mixture of 22.0 g (0.075 mole) of N-benzoyl-4-phenoxymethylpiperidine, 25 ml of 10 N aqueous sodium hydroxide solution and 175 ml of ethanol is heated under reflux for 18 hours. The reaction mixture is then evaporated in a vacuum and the residue is taken up in diethyl ether, washed with water, dried over anhydrous sodium sulfate and the solvent then evaporated off. There are obtained 12.0 g of 4-phenoxymethylpiperidine (84% of theory); m.p. 42°–43° C.

(c) Variant III:

(i) The 4-chloromethylpiperidine hydrochloride used as starting material is prepared as follows:

To a solution of 58 ml of thionyl chloride in 250 ml of chloroform, there is added dropwise a solution of 45 g (0.39 mole) of 4-hydroxymethylpiperidine in 200 ml of chloroform. After stirring for 1 hour under reflux, the reaction mixture is evaporated in a vacuum and the residue is triturated with diethyl ether. There are obtained 54.2 g of 4-chloromethylpiperidine hydrochloride (88% of theory); m.p. 130°–132° C.

(ii) To a mixture of 28 ml of 30% sodium methanolate solution and 50 ml methanol, there are added 14.1 g (0.15 mole) of phenol. The reaction mixture is evaporated, mixed with 50 ml of N,N-dimethyl formamide and 7.8 g (0.05 mole) of 4-chloromethylpiperidine hydrochloride and heated for 18 hours at 70°–80° C. After cooling, the reaction mixture is mixed with diethyl ether, washed with water and dilute aqueous sodium hydroxide solution, dried over anhydrous sodium sulfate and evaporated in a vacuum. There are obtained 3.1 g of 4-phenoxymethylpiperidine (32% of theory); m.p. 41°–42° C.

EXAMPLE 2

4-(2-Nitrophenoxymethyl)-piperidine

A mixture of 23.0 g (0.2 mole) of 4-hydroxymethylpiperidine, 31.5 g (0.2 mole) of 2-chloronitrobenzene, 11.8 g (0.21 mole) of potassium hydroxide and 200 ml of dioxane is heated to 70° C. for 3 days. The reaction mixture is then evaporated in a vacuum and the residue is taken up in diethyl ether, washed with water, extracted with dilute hydrochloric acid, rendered alkaline and the aqueous mixture extracted with diethyl ether. After evaporation of the solvent, there are obtained 10.5 g of 4-(2-nitrophenoxymethyl)-piperidine (22% of theory); b.p. 130°–132° C./0.01 mm. Hg.

EXAMPLE 3

In a manner analogous to that described in Example 1b, Variant II, there are obtained, by hydrolysis of the starting materials, the compounds set out in the following Table:

TABLE

| Starting compound | m.p. °C. | End product | b.p., °C. 0.01mm.Hg | m.p., °C. |
|---|---|---|---|---|
| N-benzoyl-4-(2-bromo-phenoxymethyl)-piperidine | oil | 4-(2-bromophenoxy-methyl)-piperidine | 142–144 | — |
| N-benzoyl-4-(2-chloro-phenoxymethyl)-piperidine | 95–97 | 4-(2-chlorophenoxy-methyl)-piperidine | 130–133 | — |
| N-benzoyl-4-(3-chloro-phenoxymethyl)-piperidine | oil | 4-(3-chlorophenoxy-methyl)-piperidine | 132–134 | — |

TABLE-continued

| Starting compound | m.p. °C. | End product | b.p., °C. 0.01mm.Hg | m.p., °C. |
|---|---|---|---|---|
| N-benzoyl-4-(4-chloro-phenoxymethyl)-piperidine | 103–104 | 4-(4-chlorophenoxy-methyl)-piperidine | 129–131 | 48–50 |
| N-benzoyl-4-(2-fluoro-phenoxymethyl)-piperidine | 112–114 | 4-(2-fluorophenoxy-methyl)-piperidine | 118–120 | — |
| N-benzoyl-4-(4-fluoro-phenoxymethyl)-piperidine | 74–76 | 4-(4-fluorophenoxy-methyl)-piperidine | 116–118 | 35–37 |
| N-benzoyl-4-(2-methoxy-phenoxymethyl)-piperidine | 96–98 | 4-(2-methoxy-phenoxymethyl)-piperidine | 135–137 | — |
| N-benzoyl-4-(3-methoxy-phenoxymethyl)-piperidine | oil | 4-(3-methoxy-phenoxymethyl-piperidine | 134–137 | — |
| N-benzoyl-4-(4-methoxy-phenoxymethyl)-piperidine | 97–98 | 4-(4-methoxy-phenoxymethyl)-piperidine | 142–144 | — |
| N-benzoyl-4-(2-n-butoxy-phenoxymethyl)-piperidine | oil | 4-(2-n-butoxy-phenoxymethyl)-piperidine | 146–148 | — |
| N-benzoyl-4-(2-methyl-phenoxymethyl)-piperidine | 92–94 | 4-(2-methyl-phenoxymethyl)-piperidine | 120–122 | — |
| N-benzoyl-4-(3-methyl-phenoxymethyl)-piperidine | 81–82 | 4-(3-methyl-phenoxymethyl)-piperidine | 115–118 | — |
| N-benzoyl-4-(4-methyl-phenoxymethyl)-piperidine | 118–120 | 4-(4-methyl-phenoxymethyl)-piperidine | 115–118 | 42–44 |
| N-benzoyl-4-(2-n-propyl-phenoxymethyl)-piperidine | oil | 4-(2-n-propyl-phenoxymethyl)-piperidine | 125–127 | — |
| N-benzoyl-4-(2-ethyl-phenoxymethyl)-piperidine | oil | 4-(2-ethyl-phenoxymethyl)-piperidine | 126–128 | — |
| N-benzoyl-4-[2-(2-butyl-phenoxymethyl]-piperidine | oil | 4-[2-(2-butyl)-phenoxymethyl]-piperidine | 128–130 | — |

The foregoing compounds can be further reacted to produce anti-hypertensive agents in accordance with the disclosures of Applications Ser. Nos. 737,507 and 737,519 filed simultaneously herewith, the disclosures of which are incorporated herein by reference. A few representative examples include the following:

EXAMPLE 4

9-[3-(4-Phenoxymethylpiperidino)-propyl]-adenine

A mixture of 28.6 g (0.15 mole) of 4-phenoxymethyl-piperidine, 23.5 g (0.15 mole) of 1-bromo-3-chloropropane, 40.4 g (0.4 mole) of triethylamine and 150 ml of tetrahydrofuran is heated under reflux for 5 hours. After cooling, the reaction mixture is filtered, the filtrate is evaporated in a vacuum, the residue is extracted with diethyl ether and the extract is evaporated. There are obtained 33.6 g (84% of theory) of crude 3-(4-phenoxymethylpiperidino)-propyl chloride in the form of an oil which can be further used in this form. The pure compound is obtained by distillation and boils at 180°–183° C./0.4 mm Hg.

9.45 g (0.07 mole) of adenine are added to a solution of 1.6 g (0.07 mole) of sodium in 250 ml of isopropanol and the reaction mixture heated under reflux for 10 minutes. It is then cooled and 21.4 g (0.08 mole) of 3-(4-phenoxymethylpiperidino)-propyl chloride in 50 ml of isopropanol added thereto. After stirring the reaction mixture under reflux for 6 hours, it is evaporated in a vacuum, the residue is taken up in methylene chloride, the methylene chloride solution is washed with 2 N aqueous sodium hydroxide solution and subsequently with water, dried over anhydrous sodium sulfate, evaporated and the residue recrystallized from isopropanol. There are obtained 16.4 g (64% of theory) of 9-[3-(4-phenoxymethylpiperidino)-propyl]-adenine; m.p. 142°–144° C.

EXAMPLE 5

3-[2-(4-Phenoxymethylpiperidino)-ethyl]-indole

A mixture of 8.96 g (0.04 mole) of 3-(2-bromoethyl)-indole, 7.65 g (0.04 mole) of 4-phenoxymethylpiperidine, 7.76 g (0.06 mole) of N-ethyl-diisopropylamine and 100 ml of dioxane is heated under reflux for 9 hours. After cooling, the reaction mixture is filtered, the filtrate is evaporated in a vacuum and the residue is taken up in diethy ether, washed with water, dried over anhydrous sodium sulfate and evaporated. After recrystallization from isopropanol/ligroin, there are obtained 5.55 g of 3-[2-(4-phenoxymethyl)-piperidino)-ethyl]-indole (41% of theory); m.p. 113°–114° C.

It will be appreciated that the instant specification and examples are set forth by way of illustration and not limitation, and that various modifications and changes may be made without departing from the spirit and scope of the present invention.

What we claim is:

1. A 4-phenoxymethyl-piperidine of the formula

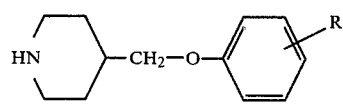

wherein R is hydrogen, halogen, nitro, alkyl of up to 4 carbon atoms or alkoxy of up to 4 carbon atoms.

2. A compound according to claim 1, wherein R is hydrogen.

3. A compound according to claim 1, wherein R is fluorine.

4. A compound according to claim 1, wherein R is chlorine.

5. A compound according to claim 1, wherein R is bromine.

6. A compound according to claim 1, wherein R is methoxy.

7. A compound according to claim 1, wherein R is n-butoxy.

8. A compound according to claim 1, wherein R is n-propyl.

9. A compund according to claim 1, wherein R is ethyl.

10. A compound according to claim 1, wherein R is 2-butyl.

11. A compound according to claim 1, wherein R is nitro.

12. A compound according to claim 1, wherein the compound is present in the form of a salt with a pharmacologically acceptable acid.

* * * * *